United States Patent [19]

Verduijn et al.

[11] Patent Number: 5,146,040
[45] Date of Patent: Sep. 8, 1992

[54] PROCESS FOR SEPARATING DIMETHYLNAPHTHALENE ISOMERS WITH ZEOLITE L AGGLOMERATES

[75] Inventors: Johannes P. Verduijn; Mechilium J. G. Janssen, both of Spijkenisse; Cornelis B. De Gruijter, Hoeck van Holland; Wicher T. Koetsier, Mijnsheerenland; Cornelis W. M. Van Oorschot, Rozenburg, all of Netherlands

[73] Assignee: Exxon Chemical Patents Inc., Linden, N.J.

[21] Appl. No.: 681,812

[22] Filed: May 10, 1991

Related U.S. Application Data

[62] Division of Ser. No. 292,704, Jan. 3, 1989, Pat. No. 5,064,630.

[30] Foreign Application Priority Data

Jan. 4, 1988 [GB] United Kingdom ............ 8800045

[51] Int. Cl.$^5$ ............................................. C07C 7/12
[52] U.S. Cl. ................... 585/825; 585/820; 585/831
[58] Field of Search ................ 585/820, 825, 831

[56] References Cited

U.S. PATENT DOCUMENTS

| | | | |
|---|---|---|---|
| 3,216,789 | 11/1965 | Breck et al. | 423/328 |
| 3,668,267 | 6/1972 | Hedge | 585/831 |
| 3,772,399 | 11/1973 | Hedge | 585/831 |
| 4,544,539 | 10/1985 | Wortel | 423/328 |
| 4,554,146 | 11/1985 | Vaughn | 423/329 |
| 4,605,637 | 8/1986 | Chang et al. | 502/64 |
| 4,701,315 | 10/1987 | Wortel | 423/328 |

FOREIGN PATENT DOCUMENTS

| | | |
|---|---|---|
| 61155215 | 7/1986 | Japan . |
| 0096479 | 12/1983 | United Kingdom . |
| 0142349 | 5/1985 | United Kingdom . |
| 0142353 | 5/1985 | United Kingdom . |
| 0142354 | 5/1985 | United Kingdom . |
| 01452355 | 5/1985 | United Kingdom . |
| 0185519 | 6/1986 | United Kingdom . |

OTHER PUBLICATIONS

Wright et al., "Localizing Active Sites in Zeolitic Catalysts; Neutron Powder Profile Analysis and Computer Simulation of Deuteropyridine Bound to Gallozeolite-L", Nature vol. 318 (1985) pp. 611–614.

Neusan et al., "Structural Studies of Gallisilicate Zeolite", New Developments in Zeolite Science and Technology, Elsevier 1986 pp. 457–463.

*Primary Examiner*—Anthony McFarlane
*Assistant Examiner*—Nhat Phan
*Attorney, Agent, or Firm*—E. F. Sherer

[57] ABSTRACT

Zeolite L in very small crystalline form is prepared by a process in which an alkaline reaction mixture comprising water, a source of silicon ($SiO_2$), a source of alkali metal (M) (KOH) and a source of aluminium ($Al_2O_3 \cdot 3H_2O$) or gallium is heated to a temperature of at least 80° C. for a period of time long enough to form zeolite L, the composition of the reaction mixture having the following molar ratios (expressed as oxides):

| | |
|---|---|
| $M_2O/SiO_2$ | 0.4 to 0.5 |
| $H_2O/M_2O$ | 15 to 30 |
| and $SiO_2/Al_2O_3$ or $Ga_2O_3$ | 5 to 11 | where M is potassium or a mixture of potassium and one or more other alkali metals. Zeolite L made by this process can be used for separating isomers of dimethylnaphthalene from one another.

2 Claims, 6 Drawing Sheets

PROCESS FOR SEPARATING DIMETHYLNAPHTHALENE ISOMERS WITH ZEOLITE L AGGLOMERATES

This is a division of application Ser. No. 292,704, filed Jan. 3, 1989, now U.S. Pat. No. 5,064,630.

This invention relates to crystalline zeolite L, its preparation and use in separations and catalysis.

Zeolite L has been known for some time and its preparation in U.S. Pat. No. 3,216,789, GB-A-1202511, U.S. Pat. No. 3,867,512, EP-A-0096479, EP-A-0142353, EP-A-0142354, EP-A-0142355, EP-A-0142347, EP-A-0142348, and EP-A-0142349. GB-A-1393365 describes zeolite AG1 which is alleged to relate to zeolite L.

Zeolite L may be used at a catalyst base in aromatization reactions as described in U.S. Pat. No. 4,104,320, EP-A-0040119, BE-A-792608, and EP-A-0142351.

EP-A-0219354 describes an improved zeolite L having a characteristic morphology and/or size and/or cation content and/or silica/alumina ratio which is particularly valuable for use as a catalyst base in hydrocarbon conversions such as aromatization. This is prepared by introducing small amounts of magnesium, calcium, barium, manganese, chromium, cobalt, nickel or zinc into the synthesis gel for zeolite L.

We have now discovered a synthesis for zeolite L which enables one to prepare very small zeolite L crystals (potassium-containing crystals) which show very good adsorptive/selective properties for 1,5; 2,6 and 2,7 dimethyl naphthalene (DMN) with an enhanced selectivity of 1,5 DMN over the other isomers of dimethyl naphthalene.

According to this invention zeolite L in very small crystalline form is prepared by a process in which an alkaline reaction mixture comprising water, a source of silicon, a source of alkali metal (M) and a source of aluminium or gallium is heated to a temperature of at least 80° C. for a period of time long enough to form zeolite L, the composition of the reaction mixture having the following molar ratios (expressed as oxides):

| | |
|---|---|
| $M_2O/SiO_2$ | 0.4 to 0.5 |
| $H_2O/M_2O$ | 15 to 30 |
| and $SiO_2/Al_2O_3$ or $Ga_2O_3$ | 5 to 11 | where M is potassium or a mixture of potassium and one or more other alkali metals. It is a feature of the invention that the formed small crystallites may be agglomerated to form particles which may easily be recovered.

In the synthesis of the zeolitic materials of the invention, the source of silicon for the reaction mixture is generally silica, and this is usually most conveniently in the form of a colloidal suspension of silica such as Ludox HS 40 available from E. I. Dupont de Nemours and Co. However, other forms such as silicates may be used.

The source of aluminium may be an alumina introduced into the reaction medium as, for example, $Al_2O_3 \cdot 3H_2O$, previously dissolved in alkali. However, it is also possible to introduce aluminium in the form of the metal, which is dissolved in alkali.

Gallium may be introduced as gallium oxide, $Ga_2O_3$ again previously dissolved in alkali. It is preferable to use a nucleating or seeding amount of preformed zeolite L in a synthesis which contains gallium. The seeds may be prepared either by a gallium or aluminium based synthesis and are typically used in an amount of 0.1 to 0.5 weight % of the reaction mixture.

The source of potassium is usually potassium hydroxide. Alternatively one can use a source of a mixture of potassium and one or more other alkali metals, for example sodium, rubidium or caesium. Usually no more than 30 mole % of potassium is replaced by an alkali metal.

In another embodiment of the invention other metals ($M^1$) may be included. Such metals include Group Ib metals, such as copper, Group II metals, for example magnesium, calcium, barium or zinc, Group IV such as lead or Group VI, VII or VIII metals such as chromium, manganese, iron, cobalt or nickel. These metals may be introduced in the form of any convenient compound, for example as an oxide, hydroxide, nitrate or sulphate.

A suitable ratio of M to $M^1$ expressed as oxides is a molar ratio $M_2O/M^1_{2/n}O$ where n is the valency of $M^1$ of 700 to 1000.

The preferred molar ratios when $M^1$ is absent are as follows:

| | |
|---|---|
| $M_2O/SiO_2$ | 0.42 to 0.48 |
| $H_2O/M_2O$ | 20 to 25 |
| and $SiO_2/Al_2O_3$ | 5 to 8, especially 6 to 7 |
| or $M_2O/SiO_2$ | 0.42 to 0.48 |
| $H_2O/M_2O$ | 20 to 25 |
| and $SiO_2/Ga_2O_3$ | 7 to 11, especially 9 to 11 |

Typical reaction mixtures will fall in the following molar ranges expressed as oxides: 4–5 $K_2O$/1.25–1.50 $Al_2O_3$/10 $SiO_2$/80–150 $H_2O$ and 4–5 $K_2O$/1.00–1.50 $Ga_2O_3$/10 $SiO_2$/80–150 $H_2O$.

When $M^1$ is present the preferred molar ratios are as follows:

| | |
|---|---|
| $(M_2O + M^1_{2/n}O)/SiO_2$ | 0.42 to 0.48 |
| $H_2O/(M_2O + M^1_{2/n}O)$ | 20 to 25 |
| $M_2O/M^1_{2/n}O$ | 800 to 900 |
| and $SiO_2/Al_2O_3$ | 5 to 8, especially 6 to 7 |
| or $(M_2O + M^1_{2/n}O)/SiO_2$ | 0.42 to 0.48 |
| $H_2O/(M_2O + M^1_{2/n}O)$ | 20 to 25 |
| $M_2O/M^1_{2/n}O$ | 800 to 900 |
| and $SiO_2/Ga_2O_3$ | 7 to 11, especially 9 to 11 |

Figure 1:
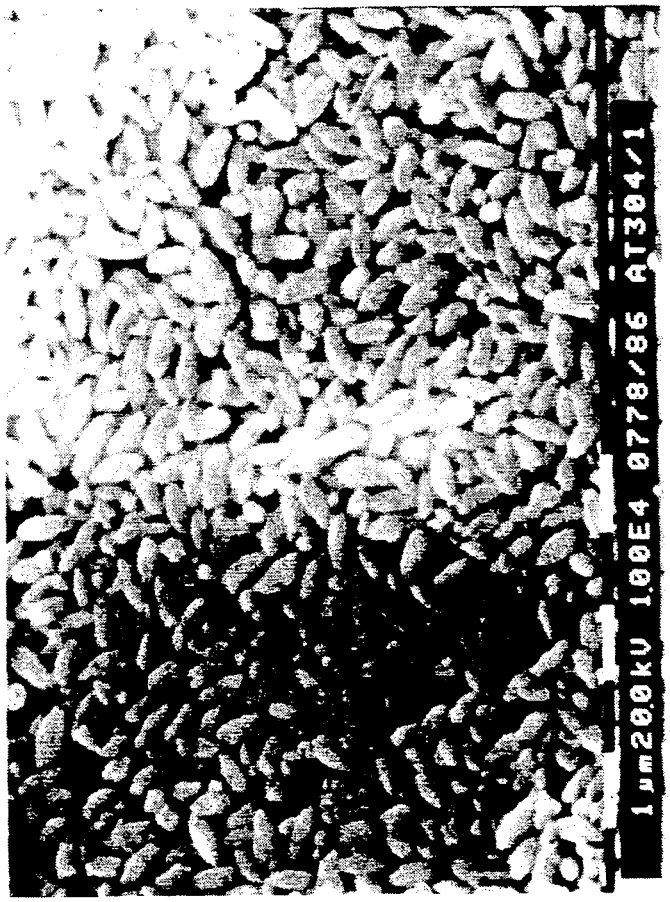
FIG. 1 is a scanning electron micrograph (SEM), at an enlargement of 10,000, of agglomerated zeolite crystals prepared in accordance with Example 1.

In order to prepare the zeolite L according to the invention, i.e. with very small KL crystals, a prepared gel is crystallised in a very alkaline/aluminium rich/low water environment. The above-described reaction mixture is a very alkaline synthesis mixture because of the high $M_2O/SiO_2$ molar ratio.

The gel is usually prepared by dissolving the aluminium or gallium compound, e.g. $Al_2O_3$, in an aqueous solution of the alkali metal (M) compound, e.g. KOH, to form a solution. This dissolution is usually achieved by boiling the aluminium compound in the aqueous solution of the alkali metal compound. After dissolution any water loss can be corrected. A separate solution comprises the silicon compound, e.g. colloidal silica, which may be diluted with water. The two solutions are then mixed, e.g. for about 2 minutes, to form the required gel. The amounts of reactants are of course chosen so that the molar ratios thereof fall within the defined limits. If a compound of another metal is also used the compound of the metal ($M^1$) can be included with the compound of the alkali metal (M) or added later.

The crystallisation is generally carried out in a sealed autoclave and thus at autogenous pressure. It is generally inconvenient, although possible, to employ higher pressures. Lower pressure will require longer crystallisation times.

Crystallisation time is related to the crystallisation temperature. The crystallisation is carried out at a temperature of at least 80° C., preferably 130° C. to 150° C. and at this temperature the crystallisation time may be from 14 to 72 hours, typically from 16 to 24 hours. Lower temperature may require longer times to achieve good yield of the desired product, whereas times of less than 16 hours are possible when higher temperatures are used. A time of 4 to 8 hours is typical for a temperature of 200° C. or greater.

Following the preparation as described above the zeolite L may be separated, washed and dried. The washing may be to a pH of more than 7, e.g. 9 to 10. Drying may be at a temperature of above 120° C., e.g. about 125° C. for at least 10 hours, e.g. about 16 hours.

It is found that the zeolite L obtained by the process of this invention (using aluminium) is extremely aluminous, for example the $Si/Al_2$ molar ratio can be as low as 4.0 to 4.5, e.g. about 4.3, whilst the K/Al atomic ratio can be close to unity.

X-ray diffraction (XRD) shows that the product is substantially XRD invisible. Analysis by scanning electron microscopy indicates that the product consists of very uniform aggregates with a length of 0.50 to 1.50, e.g. about 0.70 micrometers and with a diameter of 0.20 to 0.60, e.g. about 0.4 micrometers. Thus the size of the agglomerate is dependent on the alkalinity of the reaction mixture.

By illuminating agglomerated zeolite crystals obtained by the process of this invention with 120 kV accelerated electrons in a transmission electron microscope it was found that the crystals are typically 40 to 60 nm long and that their diameters range from 10 to 20 nm. The channels of the zeolite L crystals within the agglomerate were found all to have the same direction, plus or minus 15°. This means that there are small pores between the crystals which are about 6 to 15 nm in diameter, giving the agglomerates a three-dimensional channel system.

Accordingly this invention provides an agglomerate of crystals of zeolite L, said crystals being 30 to 70 nm long and of diameter 5 to 25 nm with pores between the crystals of 3 to 20 nm diameter. The crystals are preferably 40 to 60 nm long and of diameter 10 to 20 nm and the pores are preferably of 6 to 15 nm diameter.

The very small crystals of zeolite L produced by the process of this invention and the above defined agglomerate of crystals of zeolite L show very good absorptive/selective properties, and may be useful in organic separation. They have been found to be particularly useful in separation of 1,5; 2,6 and 2,7 dimethyl naphthalene (DMN). The 1,5 DMN shows an enhanced selectivity over the 2,6 and 2,7 isomers. Because of the very small sized crystals there is a much lower mass transfer resistance when carrying out dynamic liquid chromatography. In accordance with this invention the 1,5; 2,6 and 2,7 isomers of dimethyl naphthalene (DMN) are separated from one another by passing a stream comprising said isomers through a mass of the zeolite L produced by the process of this invention or of the above defined agglomerate of crystals of zeolite L and obtaining substantially pure 2,7 DMN, followed by substantially pure 2,6 DMN and thereafter substantially pure 1,5 DMN.

The mass of zeolite L or of the defined agglomerate of crystals of zeolite L can for example be a column or a fluidised bed and the stream comprising the isomers is pumped into the bottom of the column or fluidised bed. This stream can for example be a petroleum refinery stream. The desired isomers are obtained in substantially pure state in phased intervals from the outlet of the column or of the fluidised bed.

The zeolite L prepared by the invention may be used as a catalyst base and may be used in combination with a catalytically active metal in a wide variety of catalytic reactions. It is especially suited to catalytic applications where a low acid site strength is advantageous such as aromatisation.

The catalytically-active metal(s) may be, for example, a Group VIII metal such as platinum, or tin or germanium as described in U.S. Pat. No. 4,104,320, or a combination of platinum and rhenium as described in GB-A-2004764 or BE-A-888365. In the latter case, the catalyst may for appropriate circumstances also incorporate halogen as described in U.S. Pat. No. 4,165,276, silver as described in U.S. Pat. No. 4,295,959 and U.S. Pat. No. 4,206,040, cadmium as described in U.S. Pat. No. 4,295,960 and U.S. Pat. No. 4,231,897 or sulphur as described in GB-A-1600927.

A particularly advantageous catalyst composition incorporates from 0.1 to 6.0 wt. %, (based on the total weight of the composition), preferably from 0.1 to 1.5 wt. % platinum or palladium, since this gives excellent results in aromatisation. From 0.4 to 1.2 wt. % platinum is particularly preferred. Accordingly the invention provides a catalyst comprising the zeolite and a catalytically-active metal.

It may also be useful to incorporate into the catalyst of the invention one or more materials substantially inert under the conditions in which the catalyst is to be employed to act as a binder. Such binders may also act to improve the resistance of the catalyst to temperature, pressure and attrition.

The zeolite L of the invention may be used in a process for the conversion of a hydrocarbon feed in which the feed is contacted with a catalyst as described above under appropriate conditions to bring about the desired conversion. They may, for example, be useful in reactions involving aromatisation and/or dehydrocyclisation and/or isomerisation and/or dehydrogenation reaction. They are particularly useful in a process for the dehydrocyclisation and/or isomerisation of aliphatic hydrocarbons in which the hydrocarbons are contacted at a temperature of from 370° to 600° C., preferably 430° to 550° C., with a catalyst comprising zeolite L of the invention, preferably having at least 90% of the cations M as potassium ions, and preferably incorporating at least one Group VIII metal having dehydrogenating activity, so as to convert at least part of the aliphatic hydrocarbons into aromatic hydrocarbons.

The aliphatic hydrocarbons may be straight or branched chain acyclic hydrocarbons, and particularly paraffins such as hexane, although mixtures of hydrocarbons may also be used such as paraffin fractions containing a range of alkanes possibly with minor amounts of other hydrocarbons. Cycloaliphatic hydrocarbon such as methylcyclopentane may also be used. In a preferred embodiment the feed to a process for preparing aromatic hydrocarbons and particularly benzene comprises hexanes. The temperature of the catalytic reaction may be from 370° to 600° C., preferably 430° to 550° C. and preferably pressures in excess of atmospheric are used, for example up to 2000 KPa, more preferably 500 to 1000 KPa. Hydrogen is employed in the formation of aromatic hydrocarbons preferably with a hydrogen to feed ratio of less than 10.

The process is preferably otherwise carried out in the manner described in U.S. Pat. No. 4,104,320, BE-A-888365, EP-A-0040119, EP-A-0142351, EP-A-0145289 or EP-A-0142352.

The invention is now illustrated by the following Examples.

EXAMPLE 1

A very alkaline synthesis mixture (solutions A and B) was prepared having the molar composition 4.5 K$_2$O/0.0054 BaO/1.50 Al$_2$O$_3$/10 SiO$_2$/102 H$_2$O The two solutions A and B were mixed together; solution A (potassium aluminate solution) was as follows:
  KOH pellets (87.3%): 72.27 g
  Al(OH)$_3$ (99.9%): 29.26 g
  Water: 62.62 g
  Rinsing water: 35.18 g.
  Solution B (silicate solution) was as follows:
  Ludox HS40 (SiO$_2$): 187.82 g
  Ba(OH)$_2$ 8H$_2$O: 0.2142 g.

The Al(OH)$_3$ was dissolved by boiling and after cooling to ambient temperature the weight loss due to evaporation of water was corrected.

The two solutions A and B were then mixed for about two minutes to form a gel.

The gel was heated in a 300 ml autoclave under autogenous pressure to 150° C. and maintained at this temperature for 20 hours. The product was washed to a pH of 9.8 and subsequently dried at 125° C. for 16 hours. The product yield was 23%

$$\left(\text{product yield} = \frac{\text{weight dry product}}{\text{weight gel}} \times 100\%\right)$$

Elemental analysis showed that the zeolite product was extremely aluminous, i.e. the Si/Al$_2$ molar ratio was 4.3. The K/Al atomic ratio was 1.04.

Analysis by scanning electron micrographs (SEM) indicated that the product consisted of very uniform agglomerates with a length of about 0.7 micrometers and with a diameter of about 0.4 micrometers. The SEM at an enlargement of 10,000 is shown in FIG. 1.

The agglomerated zeolite crystals were illuminated with 120 kV accelerated electrons in a transmission electron microscope. It was found that the agglomerate consisted of tiny zeolite crystals and that the zeolite is a zeolite L. The crystals were found to be typically 40 to 60 nm long with diameters ranging from 10 to 20 nm. The channels of the zeolite L crystals within the agglomerate were found all to have the same direction, plus or minus 15°. This means that there were small pores between the crystals, approximately 6 to 15 nm in diameter, giving the agglomerates a three-dimensional channel system.

EXAMPLE 2

The zeolite L product obtained in Example 1 was tested in a static adsorption test so as to determine the distribution of a component over the liquid and the adsorbent phase. In a static adsorption test a known amount of adsorbent is equilibrated with a known amount of solution, containing the compounds to be separated. Before and after equilibration the liquid phase is analyzed mostly by gas chromotography (GC).

From experimental data of the liquid phase concentration a total hydrocarbon capacity and a so-called static separation factor is calculated. The zeolite L product, which consisted of agglomerates of nanometer sized crystals, was tested in a liquid phase static equilibrium test at 150° C. using an equimolar feed of 2.6 DMN:2.7 DMN:1.5 DMN (1:1:1) in the absence of any desorbent. As a diluent N-decane was used.

The results of this test are given in Table 1. Also in table 1, the results are shown of a liquid phase static equilibrium test in which conventionally sized zeolite L-crystals were used as an adsorbent.

TABLE 1

|  | adsorbent: conventionally sized zeolite L-crystals | adsorbent: nanometer sized zeolite L-crystals |
|---|---|---|
| 2.6/2.7 separation factor | 4.3 | 1.8 |
| 1.5/2.6 separation factor | 0.9 | 1.9 |
| Total DMN capacity, wt % | 4 | 7 |

EXAMPLE 3

Three further zeolite L products (X,Y and Z) were prepared using the following synthesis mixtures (weight of reactants in grams).

|  | X | Y | Z |
|---|---|---|---|
| KOH (87.3%) | 76.29 | 76.27 | 76.25 |
| Al(OH)$_3$ (99.9%) | 25.35 | 25.35 | 25.35 |
| H$_2$O | 75.09 | 75.10 | 75.70 |
| Rinsing water | 22.26 | 22.47 | 22.03 |

-continued

|  | X | Y | Z |
|---|---|---|---|
| Ludox HS-40 | 187.84 | 187.86 | 187.84 |
| Ba(OH)$_2$.8H$_2$O | 0.2136 | — | — |
| Weight of gel in autoclaves | 354.97 | 348.78 | 368.90 |

The procedure of Example 1 was repeated and the crystallisation took 20¼ hours at 150° C. After this aging period the autoclaves were quenched with running tap water.

The gel compositions were as follows:
X: 4.75 K$_2$O/0.0054 BaO/1.30 Al$_2$O$_3$/10 SiO$_2$/102 H$_2$O
Y: 4.75 K$_2$O/1.30 Al$_2$O$_3$/10 SiO$_2$/102 H$_2$O
Z: 4.75 K$_2$O/1.30 Al$_2$O$_3$/10 SiO$_2$/102 H$_2$O The products were washed with demineralised water. The products were dried for approximately 20 hours at 125° C. The product weights were: X 70.7 g, Y 69.9 g, Z 83 g. The product yields were: X 19.9%, Y 20.0%, Z 19.9%.

XRD: The products showed the typical XRD traces namely very broad and weak L-pattern, the peak at 205 was not present.

SEM showed that in all cases the zeolite L product has an agglomerative appearance, the size of the agglomerates is smaller than that of Example 1. This was expected since the alkalinity (K$_2$O/SiO$_2$ ratio) was increased versus that of Example 1. X,Y,Z:K$_2$O/SiO$_2$ ratio:0.425 versus H$_2$O/SiO$_2$ ratio for that of Example 1 of 0.450.

EXAMPLE 4

Two zeolite L (A and B) were prepared based on gallium instead of aluminium. The preparation synthesis mixture (weight reactants in grams) were:

|  | A | B |
|---|---|---|
| KOH (87.3%) | 77.10 | 86.73 |
| Ga$_2$O$_3$ | 28.11 | 28.12 |
| H$_2$O | 80.10 | 80.29 |
| Rinse water | 41.83 | 40.17 |
| Ludox HS-40 (SiO$_2$) | 225.43 | 225.40 |
| Seeds | 0.67 | 0.70 |

The seeds were seed of zeolite L containing potassium and a few ppm of cobalt of size 0.1 μm.

The seeds were mixed for about 5 minutes at high speed in the Ludox HS40. The gallate solutions were then added and the beakers containing the gallate solutions were then rinsed with rinse water. The rinsing water was added to the mixture and the mixtures were mixed for 3 minutes. The resulting synthesis mixtures were pourable like water.

The synthesis mixtures were divided over several containers.
A: 224.84 g in polypropylene vessel (A1)
A: 222.02 g in a stainless steel 300 ml autoclave (A2)
B: 227.58 g in a polypropylene vessel (B1)
B: 223.85 g in a stainless steel 300 ml autoclave (B2)

Those mixtures in the polypropylene vessels (A1 and B1) were crystallised at 135° C. in an oil bath and those mixtures in the stainless steel autoclave (A2 and B2) were crystallised at 135° C. in a laboratory oven.

The gel compositions (moles) were as follows:
A: 4.0 K$_2$O/Ga$_2$O$_3$/10 SiO$_2$/99 H$_2$O+0.15% seeds
B: 4.5 K$_2$O/Ga$_2$O$_3$/10 SiO$_2$/99 H$_2$O+0.15% seeds It was found that ±5 minutes after placing the containers in the oil bath at 135° C. gellation of the mixture started.

After 40 hours into heating the crystallisation was terminated. The products were washed with demineralised water and the pH's were:
A1: 10.7, B1: 10.9
A2: 10.5, B2: 10.6

After drying at 125° C. for 16 hours the weights of the recovered products were:

|  |  | yield % |
|---|---|---|
| A1 | 40.2 g | 17.9 |
| A2 | 39.9 g | 18.0 |
| B1 | 34.8 g | 15.3 |
| B2 | 37.3 g | 16.7 |

During washing a small amount (1 gram) of the product was lost; it was very difficult to recover all the product. This indicated that the product consisted of very small particles.

Calculated SiO$_2$/Ga$_2$O$_3$ Ratio (from weight of recovered product):
A1: SiO$_2$/Ga$_2$O$_3$=4.2
A2: SiO$_2$/Ga$_2$O$_3$=4.2
B1: SiO$_2$/Ga$_2$O$_3$=3.1
B2: SiO$_2$/Ga$_2$O$_3$=3.8

Figure 2:
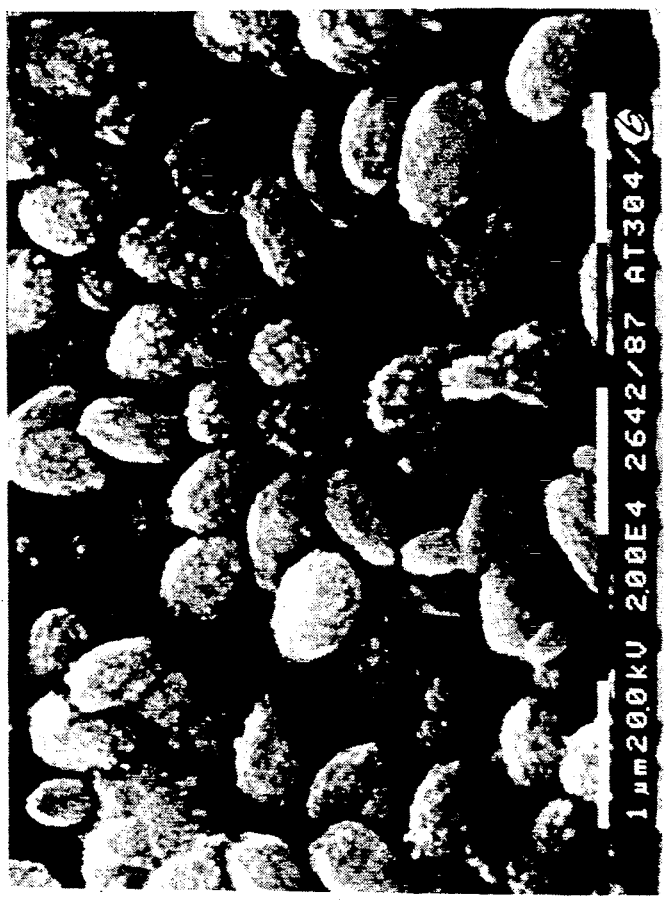
FIG. 2 is an SEM, at an enlargement of 20,000, of zeolite L prepared in a polypropylene vessel as described in Example 4.
Figure 3:
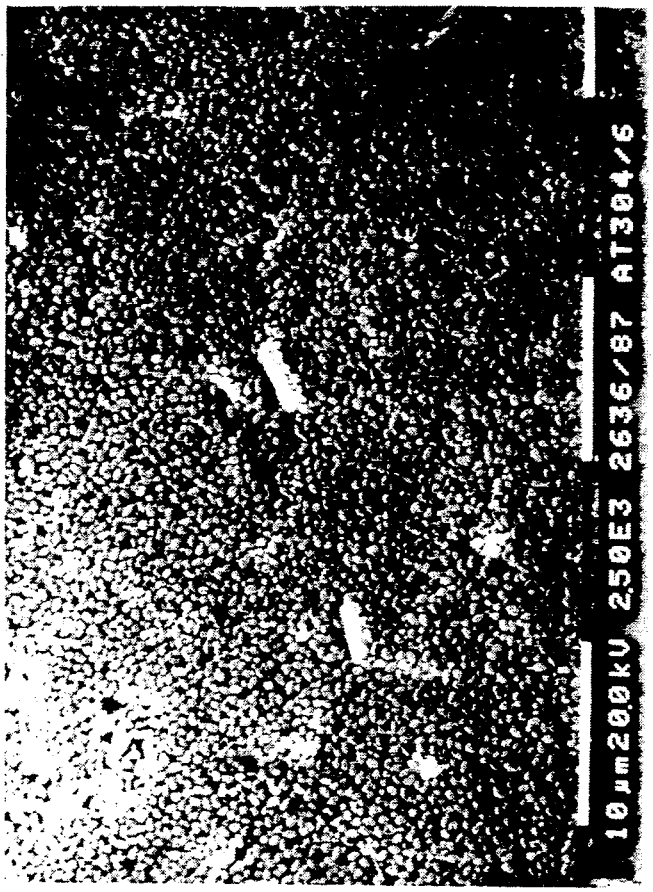
FIG. 3. is an SEM, at an enlargement of 20,000, of zeolite L prepared in a stainless steel autoclave in accordance with Example 4.

The SEM for A1 and A2 at an enlargement of 20,000 and 2,500 respective are shown in FIGS. 2 and 3.

It can be observed that there is an increase in the total DMN capacity and that there is an improved selectivity towards the 1.5 DMN isomer.

EXAMPLE 5

CHARACTERIZATION BY LIQUID CHROMATOGRAPHY (LC) TESTS

In the dynamic LC test a desorbent, a single component or a mixture of components, is flown at a constant rate through a column filled with the adsorbent particles.

In this case, at zero time a pulse of 2.6, 2.7 or 1.5 DMN was injected into a stream of n-decane containing 3 weight % of o-xylene, the adsorbent being zeolite L crystals.

The concentration of the eluting component was recorded as a function of the elution volume.

Figure 4A:
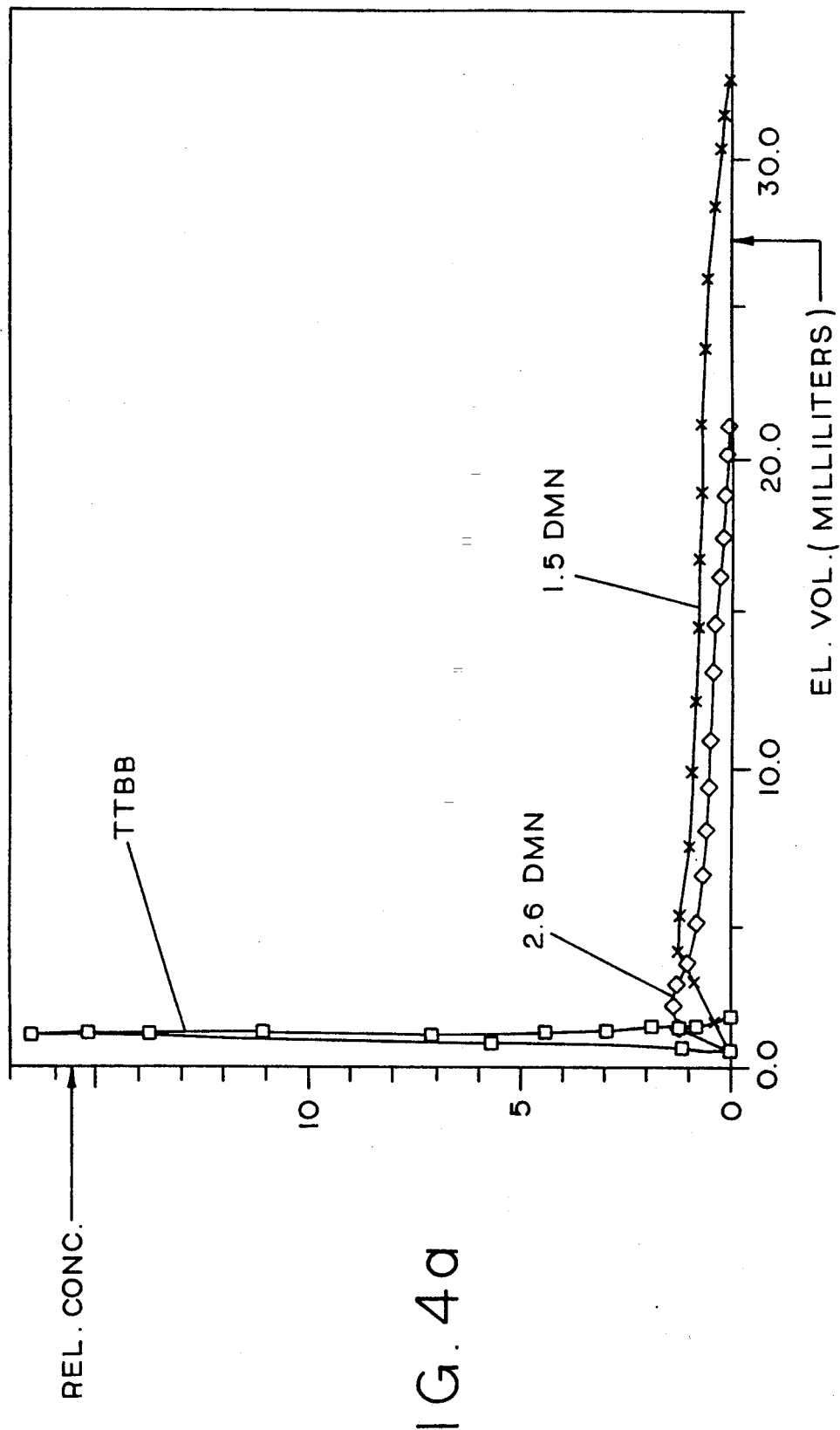
FIG. 4a shows the relative concentration versus elution volume for conventionally sized zeolite L crystals at a temperature of 192° C. based upon the liquid chromatography tests described in Example 5, using a 3 wt. % solution of o-xylene in N-decane.
Figure 4B:
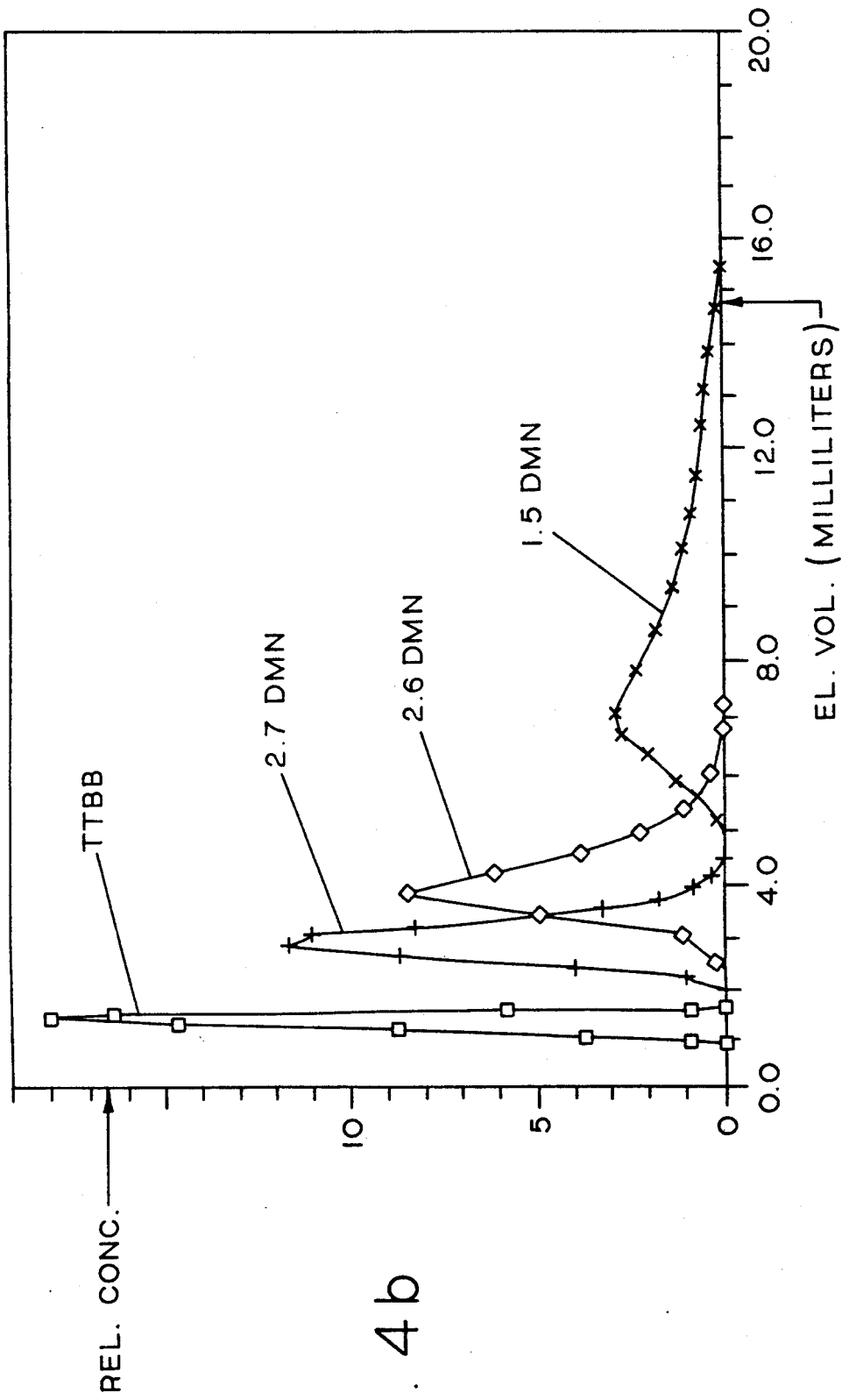
FIG. 4b depicts the relative concentration versus elution volume for nanometer sized zeolite L crystals obtained by the process of Example 1 at 192° C., based upon the liquid chromatography tests described in Example 5, using a 3 wt. % solution of o-xylene in N-decane.
Figure 4C:
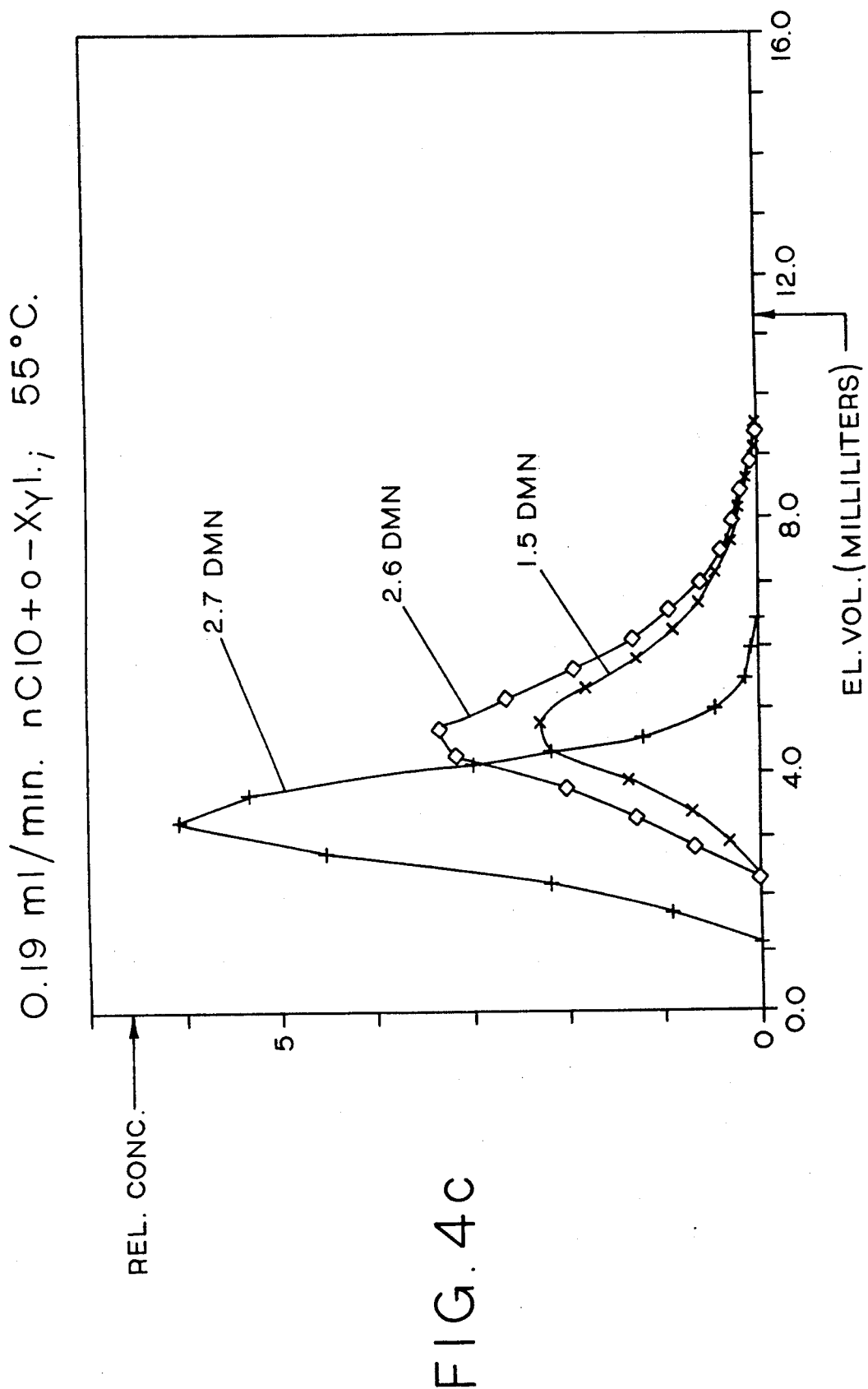
FIG. 4c depicts the relative concentration versus elution volume for nanometer sized zeolite L crystals obtained by the process of Example 1 at 55° C., based upon the liquid chromatography tests described in Example 5, using a 3 wt. % solution of o-xylene in N-decane.

The results are shown in FIGS. 4a, 4b and 4c in which the pump discharge is 0.2 ml/min and the desorbent is 3 wt % solution of o-xylene in N-decane.

In FIG. 4a, the relative concentration versus elution volume is given for conventionally sized zeolite L crystals at a temperature of 192° C.

In FIG. 4b, the relative concentration versus elution volume is given for nanometer sized zeolite L crystals obtained by the process of Example 1 at 192° C.

In FIG. 4c, the relative concentration versus elution volume is given for nanometer sized zeolite L crystals obtained by the process of Example 1 at 55° C. In all these examples a 3 wt % solution of o-xylene in N-decane was used as desorbent. It can be observed that
 (1) for conventionally sized zeolite L crystals 1.5 and 2.6 DMN elute as broad, ill-shaped peaks;
 (2) for nanometer sized zeolite L crystals 1.5 and 2.6 DMN elute as relatively sharp peaks; and
 (3) even at 55° C. relatively sharp peaks are observed for nanometer sized zeolite L crystals.

From these observations it can be concluded that a significant reduction of the mass transfer resistance is achieved in a dynamic separation process when a zeolitic adsorbent is used which has an effective crystal size which is much smaller than the usual crystal size of one micron. Moreover, this reduced mass transfer resistance allows one to employ a lower operating temperature in a dynamic separation process.

We claim:

1. A process for the separation of the 1,5; 2,6 and 2,7 isomers of dimethyl naphthalene (DMN) from one another by passing a stream comprising said isomers through an agglomerate of crystals of zeolite L, said crystals being 30 to 70 nm long and of diameter 5 to 25 nm with pores between the crystals of 3 to 20 nm diameter and obtaining substantially pure 2,7 DMN, followed by substantially pure 2,6 DMN and thereafter substantially pure 1,5 DMN.

2. The process recited in claim 1 wherein said crystals of zeolite L are prepared from an alkaline reaction mixture comprising water, a source of silicon, a source of alkali metal (M) and a source of aluminum or gallium having the following molar ratios (expressed as oxides):

| | | |
|---|---|---|
| | $M_2O/SiO_2$ | 0.4 to 0.5; |
| | $H_2O/M_2O$ | 15 to 30; |
| and either | $SiO_2/Al_2O_3$ | 5 to 8, |
| or | $SiO_2/Ga_2O_3$ | 7 to 11 | where M is potassium or a mixture of potassium and one or more other alkali metals, which is heated to a temperature of at least 80° C. for a period of time long enough to form zeolite L which is substantially invisible to x-ray diffraction.

* * * * *